United States Patent [19]

Suga

[11] 4,069,019

[45] Jan. 17, 1978

[54] SEAL STRUCTURE FOR TANK LID OF SPRAY CORROSION TESTER

[76] Inventor: Shigeru Suga, Yoyogi 5-20-2, Shibuya, Tokyo, Japan

[21] Appl. No.: 723,935

[22] Filed: Sept. 16, 1976

[51] Int. Cl.² ............... G01N 17/00; B65D 53/06; F16J 15/14
[52] U.S. Cl. .................................. 23/253 C; 49/485; 220/378; 277/135
[58] Field of Search ............ 23/253 C; 21/92, 95, 21/103; 49/485, 489; 220/217, 225, 228, 354, 358, 378; 277/135; 217/105

[56] References Cited

U.S. PATENT DOCUMENTS

| 1,244,722 | 10/1917 | Finne | 277/135 |
|---|---|---|---|
| 1,585,512 | 5/1926 | Roades | 220/228 X |
| 1,591,432 | 7/1926 | Noble | 220/228 X |

OTHER PUBLICATIONS

Industrial Test Cabinets Bulletin 401, Apr., 1963, pp. 1-4.

Primary Examiner—Morris O. Wolk
Assistant Examiner—Roger F. Phillips
Attorney, Agent, or Firm—Wenderoth, Lind & Ponack

[57] ABSTRACT

A spray corrosion test apparatus comprising an open topped test tank and a lid to cover the top of said test tank, said test tank having provided around the top edge of the side wall thereof a groove between the inner and outer surfaces of the wall thereof, said groove being adapted to receive the edge of said lid, the portion of said side wall defining the outer surface of said groove being higher than the inner surface, said groove being filled with a flexible porous insert of a water absorbing material up to the level of said inner surface. When said insert is sufficiently wetted with water, the tank and lid form an improved seal and the environment within the tank is resistant to fluctuation thereby providing test data of excellent reproducibility.

4 Claims, 3 Drawing Figures

SEAL STRUCTURE FOR TANK LID OF SPRAY CORROSION TESTER

BACKGROUND OF THE INVENTION AND PRIOR ART

Spray corrosion testers are extensively employed to test the corrosive property of coatings such as paint or rust-proof oil films, which coatings may be applied to metal surfaces such as aluminum, iron and stainless steel plates and the like.

In the conventional spray tester, a corrosive aqueous solution containing about 5% salt water and, if necessary, cupric salts, are sprayed through a nozzle over a test piece placed on a suitable holder provided within the tester tank. The temperature and relative humidity within the tank is maintained at a constant level. The extent of rust generation on the surface of the test piece is then examined.

The test apparatus is, of course, assembled from corrosion-resistant materials.

The results of the tests, however, are greatly affected by the nature of the spray in the test apparatus, atmospheric conditions and the construction of the test apparatus itself.

Typically, the following test conditions are required.

1. The temperature ranges from 35° to 50° C, and tolerance should be within ±1° C.
2. The amount of spray received on the holder carrying the test piece should be between 1 and 2 cc/80cm$^2$ per one hour and be uniformly distributed.
3. The salt concentration in the spray varies since salt concentration in the solution within the salt water tank increases with lapse of time. Moreover, the spray itself is quite concentrated and periodic inspection is required to insure uniformity of sale concentration in view of the foregoing considerations.
4. In order that drops of the solution which adhere to the inner surface of the test tank lid not directly fall on the test piece, the lid must be tilted.

Further, the lid of the tester tank is required to have a structure capable of being quickly opened and closed to observe the test piece during or after the test. Also in order to prevent leakage of the spray, the lid must form a perfect seal with the tank.

A typical seal of the prior art is shown in FIG. 1, wherein the lower edge of lid 2 is immersed in a water pool provided in a groove provided around the circumference of the tester tank.

This prior art apparatus, however, has the following drawbacks:

1. In the water seal around the circumference of the tank, a gap is naturally formed between the tank and the lower edge of the lid by a rubber gasket provided as a buffer between the lid and the groove, thereby permitting water to flow between the outer and inner sides of the lid, so that heated water from the inner side becomes admixed with the water in the outer side. Consequently, heat from the tank is lost and the temperature in the area of the seal is between atmospheric temperature and the temperature of the air within the bulk of the tank. This temperature differential within the tank is obviously undesirable.

In a typical case, where atmospheric temperature is 25° C and the temperature inside the tank is 35° C, the temperature difference within the tank may be as high as 5° C unless the flow of water is stopped.

2. In view of the foregoing, with a conventional water seal, the lid and the adjacent wall area are cooled, resulting in the hydroextraction of the atmosphere in the area around the lid and adjacent wall areas inside the tank, thereby increasing the salt concentration of the spray.

3. With the cooling of the lower side of the lid, the surrounding atmosphere is disturbed and this increases the descending air stream in comparison with the flow of air in the center of the tank. This results in a loss of uniformity of spray distribution at the outer portions of the tank, in comparison with the inner portions. Simultaneously, the temperature differential of the test piece holder is increased.

It will be seen from the foregoing, that there is a close relationship between the above-discussed factors and, consequently, it is difficult to control said factors and this often results in great fluctuations in spray test data.

OBJECT OF THE INVENTION

The object of the present invention is to overcome these difficulties and thereby provide a test apparatus having superior reproducibility of data.

BRIEF SUMMARY OF THE INVENTION

The present spray corrosion test apparatus comprises an open topped test tank and a lid having vertically depending sides to cover the top of said tank, said test tank having provided around the top edge of its vertical wall a horizontal, upwardly open channel, said channel being adapted to receive the edge of the vertically depending sides of said lid. The height of the outer vertical wall of the channel is higher than the inner vertical wall of said channel and said channel is filled with a flexible porous insert of a water absorbing material up to the level of the inner vertical wall of the channel. Consequently the temperature differential between the inner and outer portions of the tank is minimized. Thus, for example, where the temperature of water in the channel is 33.5° C on the inner side, the temperature of the water on the outside is 29.5° C. This results in a small temperature differential and thus provides considerable insulation effect.

After extensive experimentation, it is now possible to realize a water seal having such unexpected effects.

DETAILED DESCRIPTION OF THE INVENTION

The embodiment of this invention and the prior art will now be described with reference to the accompanying drawings.

Figure 1:
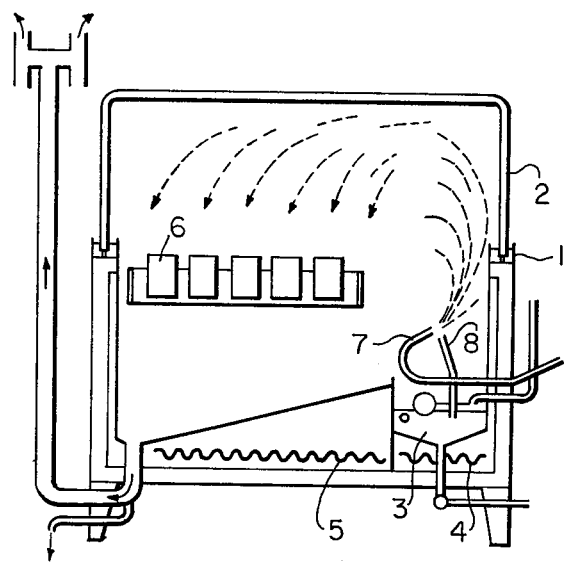
FIG. 1 is a sectional elevation view of a conventional spray corrosion tester.
Figure 2:
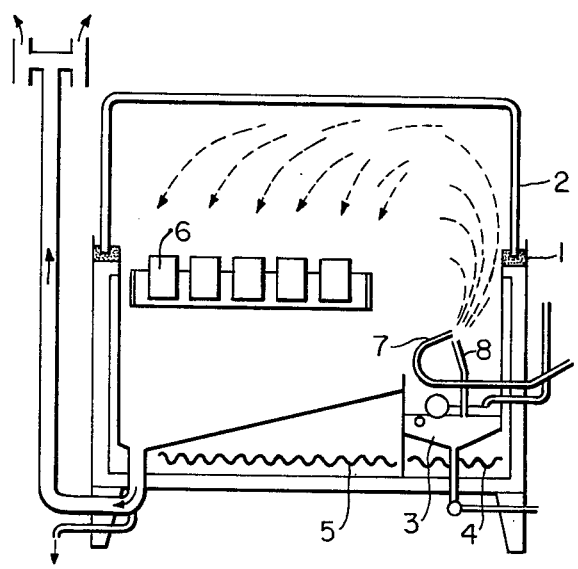
FIG. 2 is a sectional elevation view of the spray corrosion tester of the present invention.
Figure 3:
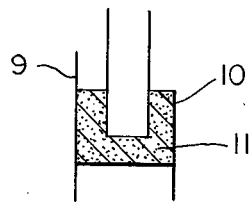
FIG. 3 is a fragmentary enlarged scale view of the seal of the present invention.

With reference to FIGS. 1 and 2, 1 represents the upper edge of the test tank apparatus, 2 represents the lid of the test tank, 3 represents the salt water tank, 4 represents the salt water tank heater, 5 represents the test apparatus heater, 6 represents the test piece holder, 7 represents the air nozzle and 8 represents the fluid supply nozzle. With reference to FIG. 3, 9 represents the tank outer wall, 10 represents the tank inner wall and 11 represents the porous insert, e.g. sponge rubber.

The distinctive feature of this invention is that the level of the outer wall 9 of the groove or channel at the top of the tester tank, which is adapted to receive the lid of the tester tank, is higher than the inner wall of said channel 10. In said channel, is inserted a flexible, water absorbing, porous material, and said flexible, porous material fills said groove up to the level of the inner wall. Water is then poured onto said porous insert and then the lid is closed, thereby forming a perfect seal.

By the term flexible is meant any material which is capable of being deformed by the weight of the lid.

Suitable materials for said porous insert include urethane foam or sponge rubber.

As is evident from FIG. 3, outer wall 9 is higher than inner wall 10. The space between the walls 9 and 10 is filled with a foam 11 such as sponge rubber which is wetted with water. Inner wall 10 of the groove is level with the top of the foam insert. By closing the lid, the sponge is displaced downwardly.

Since the outer wall is higher than the inner wall, no water will flow past the outer wall. When the lid is closed, the displaced water is collected in the recessed area of contact between the lid and the insert, thereby providing a water seal effect and preventing leakage from the spray of the apparatus. The insert also serves as a cushion to relieve shock at the time of opening and closing the lid.

Further, since water is absorbed by the insert, there is almost no movement of water and hence no movement of heat. Thus, the temperature in the tank is in equilibrium with the inner wall portion. It will thus be seen, that it is possible to obtain reduction of heat loss and improved conditions in the environment of the inner surface of the lid, by use of the instant seal, thus minimizing the aforementioned various problems.

Further, the amount of spray and temperature distribution thereof are improved as shown in Tables 1 and 2.

Table 1

|  |  | Amount of spray (per 80 cm$^2$) | Temperature |
| --- | --- | --- | --- |
| Prior art | Center of tank | 1.2 ml/h | 35 ± 1° C |
|  | Near inner wall | 2.0 ml/h | 35 ± 1° C 2° C |
| Present Invention | Center of tank | 1.5 ml/h | 35 ± 1° C |
|  | Near inner wall | 1.5 ml/h | 35 ± 1° C |

Table 2

|  | Change of salt concentration | |
| --- | --- | --- |
|  | Initial stage | After 100 hour run |
| Prior art | 5% | 5.5% |
| Present Invention | 5% | 5 % |

It is apparent that the foregoing improved seal is applicable to any shape testing tank, e.g. cylindrical, rectangular, etc. as long as the above described seal structure is formed. Rectangular tanks are somewhat more conventional, however.

We claim:

1. In a spray corrosion test apparatus comprising an open topped test tank and a lid having vertically depending sides to cover the top of said tank, said test tank having provided around the top edge of its vertical wall a horizontal upwardly open channel, said channel being adapted to receive the edge of the vertically depending sides of said lid, the improvement wherein the height of the outer vertical wall of the channel is higher than the inner vertical wall of said channel, said channel being filled with a flexible porous insert of a water absorbing material up to the level of the inner vertical wall of the channel.

2. A spray corrosion test apparatus according to claim 1 wherein sponge rubber is used as said flexible, porous water absorbing material inserted in said channel.

3. A spray corrosion test apparatus according to claim 1 wherein polyurethane foam is used as said flexible, porous water absorbing material inserted in said channel.

4. A spray corrosion test apparatus according to claim 1 wherein said tank and lid are of rectangular shape.

* * * * *